US00PP10224P

United States Patent [19]

Glicenstein

[11] Patent Number: Plant 10,224

[45] Date of Patent: Feb. 3, 1998

[54] CHRYSANTHEMUM PLANT NAMED 'CANTON'

[75] Inventor: Leon Glicenstein, Alva, Fla.

[73] Assignee: Yoder Brothers Inc., Barberton, Ohio

[21] Appl. No.: 772,493

[22] Filed: Dec. 23, 1996

[51] Int. Cl.[6] ..... A01H 5/00

[52] U.S. Cl. ..... Plt./74.1

[58] Field of Search ..... Plt./74.1, 82.4

*Primary Examiner*—Howard J. Locker

*Attorney, Agent, or Firm*—C. A. Whealy

[57] ABSTRACT

A distinct cultivar of Chrysanthemum plant named 'Canton', characterized by its rounded uniform plant habit; medium-sized anemone spray-type inflorescences that are 5.1 to 5.7 cm in diameter; attractive lavender quilled ray florets and light yellow to yellow disc florets; numerous inflorescences per plant; and good postproduction longevity with inflorescences maintaining good substance and color for about three weeks in an interior environment.

3 Drawing Sheets

The present invention relates to a new and distinct cultivar of Chrysanthemum plant, botanically known as *Dendranthema grandiflora* and referred to by the cultivar name Canton.

The new cultivar is a product of a planned breeding program conducted by the inventor in Salinas, Calif. The objective of the breeding program is to create new Chrysanthemum cultivars having inflorescences with desirable inflorescence forms and floret colors and good post-production longevity.

The new cultivar originated from a cross made by the inventor in November, 1992, of two unnamed proprietary seedling selections.

The cultivar Canton was discovered and selected by the inventor as a flowering plant within the progeny of the stated cross in a controlled environment in Salinas, Calif., in August, 1993. The selection of this plant was based on its desirable inflorescence form and floret colors and good post-production longevity.

Asexual reproduction of the new cultivar by terminal cuttings taken in a controlled environment in Salinas, Calif., has shown that the unique features of this new Chrysanthemum are stable and reproduced true to type in successive generations.

The cultivar Canton has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Canton'. These characteristics in combination distinguish 'Canton' as a new and distinct cultivar:

1. Rounded uniform plant habit.
2. Medium-sized anemone spray-type inflorescences that are 5.1 to 5.7 cm in diameter.
3. Attractive lavender quilled ray florets and light yellow to yellow disc florets.
4. Numerous inflorescences per plant.
5. Good postproduction longevity with inflorescences maintaining good substance and color for about three weeks in an interior environment.

The new Chrysanthemum is similar in ray floret color to the Chrysanthemum cultivar Rochelle (disclosed in U.S. Plant Pat. No. 7,768). However in side-by-side comparisons in Salinas, Calif., under commercial practice, plants of the new Chrysanthemum differed from plants of the cultivar Rochelle in the following characteristics:

1. Leaves of plants of the new Chrysanthemum have parallel sinuses between lateral lobes whereas plants of the cultivar Rochelle have divergent sinuses between lateral leaf lobes.
2. Plants of the new Chrysanthemum have anemone quill spray-type inflorescences whereas plants of the cultivar Rochelle have spoon daisy spray-type inflorescences.
3. Plants of the new Chrysanthemum have larger inflorescences than plants of the cultivar Rochelle.
4. Ray florets of plants of the new Chrysanthemum are lighter in color than ray florets of plants of the cultivar Rochelle.

The accompanying photographs illustrate the overall appearance of the new cultivar.

The first sheet is a colored photograph comprising a side perspective view of a typical flowering plant of 'Canton'. This photograph shows the colors as true as it is reasonably possible to obtain in colored reproductions of this type. Floret and foliage colors in the photograph may differ from the actual colors due to light reflectance.

The second sheet is a black and white photograph comprising a top perspective view of inflorescences of the cultivar Canton showing left to right: adaxial, abaxial and lateral surfaces.

The third sheet is a black and white photograph comprising a top perspective view of the abaxial (top of photo) and adaxial (bottom of photo) surfaces of leaves of the cultivar Canton at three different stages of development, left to right: mature, intermediate and immature, showing the differences in size and lobation development.

In the following description, color references are made to The Royal Horticultural Society Colour Chart except where general terms of ordinary dictionary significance are used. The following observations and measurements describe plants grown in Leaminton, Ontario, Canada, under greenhouse conditions which approximate those generally used in commercial potted chrysanthemum production. Four unrooted cuttings were directly stuck in a 15-cm container. Measurements and numerical values represent averages for a minimum of four typical flowering containers.

Botanical classification: *Dendranthema grandiflora* cultivar Canton.

Commerical classification: Anemone quill spray-type pot Chrysanthemum.

Parentage:

*Male or pollen parent.*—Unnamed propietary seedling selection.

*Female or seed parent.*—Unnamed propietary seedling selection.

Propagation:

*Type.*—Terminal tip cuttings.

*Time to rooting.*—Seven to ten days with soil temperatures of 21C.

*Rooting habit.*—Fine, fibrous and well-branched.

Plant description:

*Appearance.*—Perennial herbaceous anemone quill spray-type pot Chrysanthemum. Stems initially upright, then outwardly curving giving a rounded appearance to the plant. Uniform habit and freely branching. Five to seven lateral branches develop after removal of terminal apex (pinching).

*Plant height.*—18 to 23 cm.

*Foliage description.*—Leaf arrangement: Alternate. Leaf size, fully expanded. Length: About 7 cm. Width: About 4.5 cm. Leaf apex: Mucronate. Leaf base: Attenuate. Leaf margin: Palmately lobed, sinuses parallel. Leaf texture: Abaxial and adaxial surfaces slightly pubescent. Veins prominent on abaxial surface. Color: Young foliage adaxial surface: 147A. Young foliage abaxial surface: 147B. Mature foliage adaxial surface: 147A. Mature foliage abaxial surface: 147B. Venation abaxial surface: 147B. Venation adaxial surface: 147B.

Inflorescence description:

*Appearance.*—Anemone spray-type inflorescence form with quilled-shaped ray florets. Inflorescences borne on terminals above foliage, arising from leaf axils. Disk and ray florets arranged acropetally on a capitulum.

*Flowering response.*—Under natural conditions, plants flower in the autumn/winter in the Northern Hemisphere. At other times of the year, inflorescence initiation and development can be induced under short day/long night conditions (at least 13.5 hours of darkness). Plants exposed to 1.5 to 2 weeks of long day/short night conditions after planting followed by photoinductive short day/long night conditions flower about 46 to 50 days later.

*Postproduction longevity.*—In an interior environment, inflorescences will maintain good color and substance for about three weeks.

*Quantity of inflorescences.*—About 5 inflorescences per flowering lateral stem, or 25 to 35 inflorescences per plant.

*Inflorescence size.*—Diameter 5.1 to 5.7 cm. Depth (height): About 1 cm. Diameter of disc: About 2 cm.

*Ray florets.*—Shape: Quilled, straight, very long corolla tube. Size: Length: About 2.5 cm. Width: About 3 mm. Apex: Rounded. Margin: Fused quill tube. Texture: Smooth, glabrous. Orientation: Slightly upright, positioned about 30° to the peduncle. Number of ray florets per inflorescence: About 24. Color: Adaxial surface: 75B/75C, base white. Abaxial surface: 75B, base white.

*Disc florets.*—Shape: Enlarged tubular, apex dentate. Size: Length: About 9 mm. Width: Apex: About 2 mm. Base: About 1 mm. Number of disc florets per inflorescence: About 172. Color: Immature: 154A. Mature: Apex: Light yellow to yellow. Base: 154A.

*Peduncle.*—Aspect: Flexible, angled about 45° to the stem. Length: First peduncle: About 3 cm. Fourth peduncle: About 6 cm. Texture: Pubescent. Color: 143A.

*Reproductive organs.*—Androecium: Present on disc florets only. Anther color: 12A. Pollen: Moderate to low, 13A in color. Gynoecium: Present on both ray and disc florets.

Disease resistance: No known Chrysanthemum diseases observed to date on plants grown under commercial greenhouse conditions.

Seed production: Seed production has not been observed.

It is claimed:

1. A new and distinct cultivar of Chrysanthemum plant named 'Canton', as illustrated and described.

* * * * *

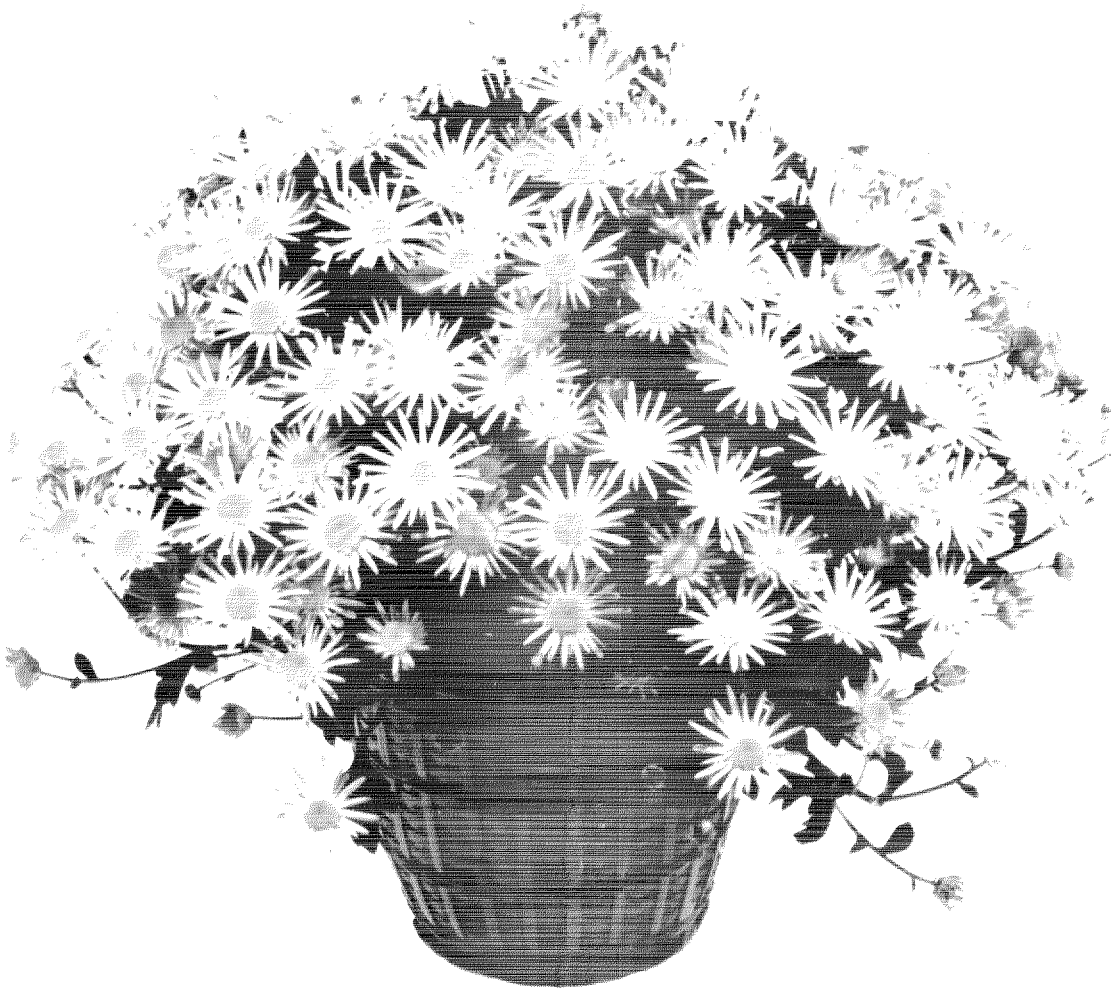

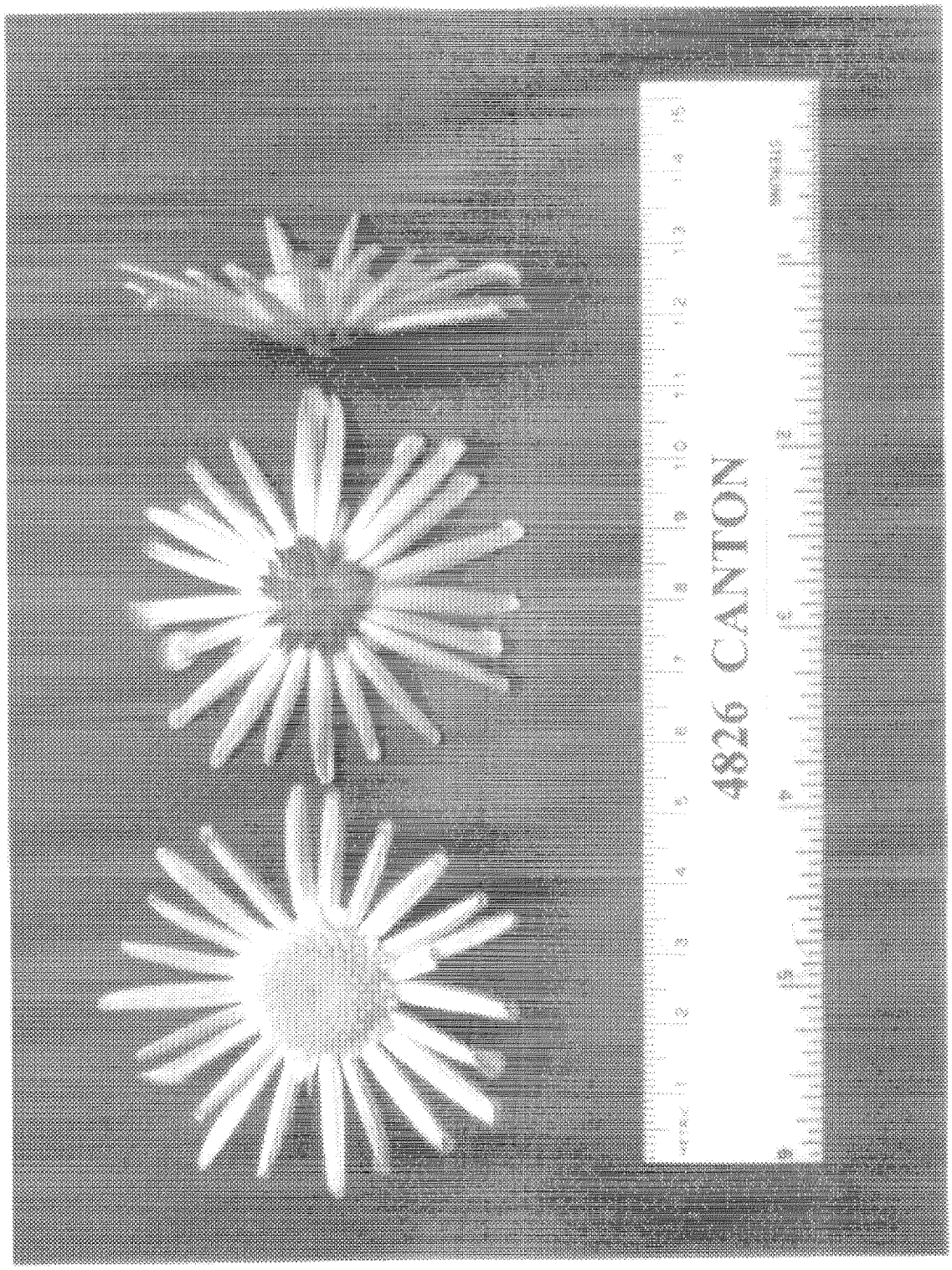
4826 CANTON

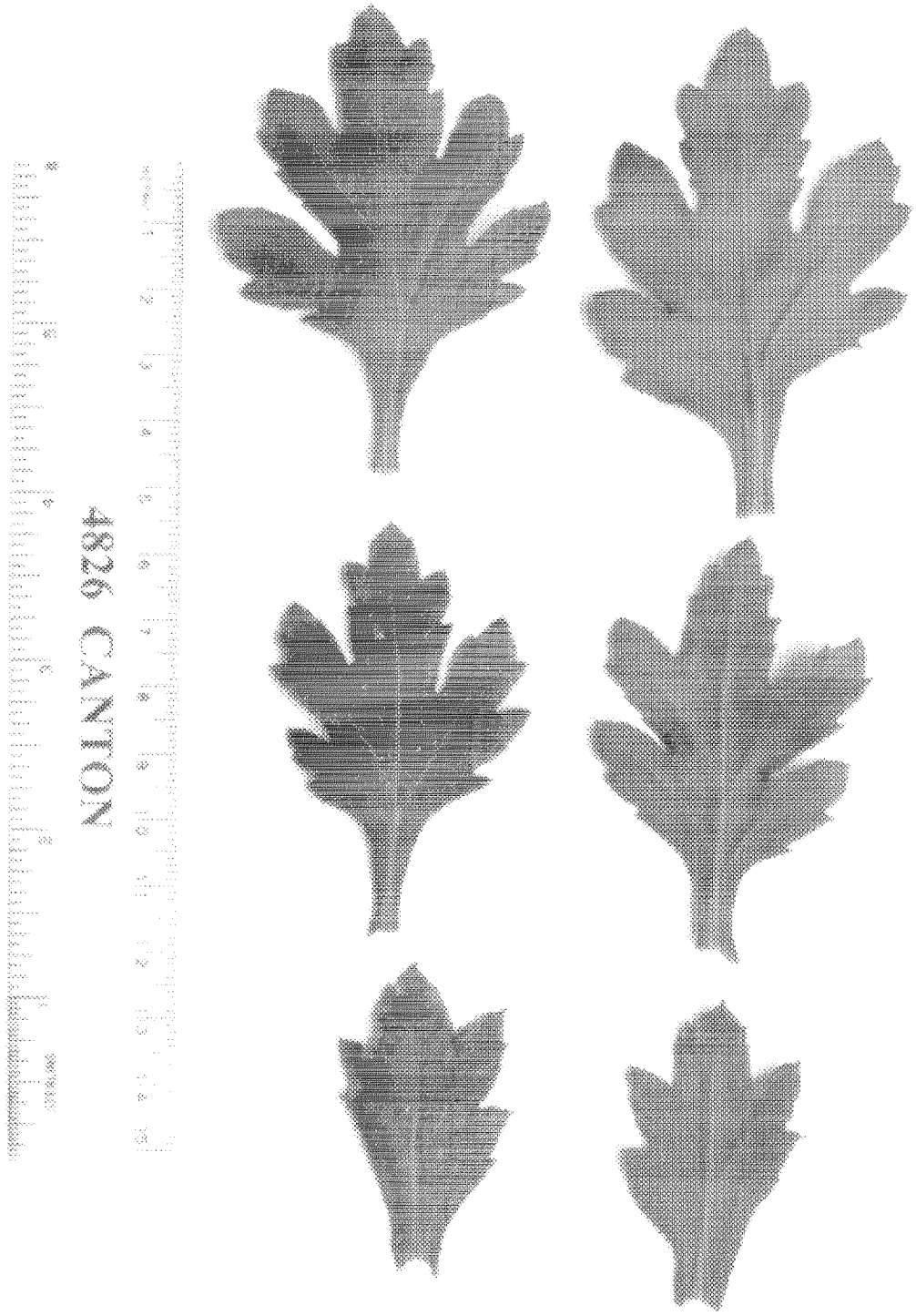
4826 CANTON